(12) United States Patent
Marshall et al.

(10) Patent No.: US 9,282,712 B1
(45) Date of Patent: Mar. 15, 2016

(54) WHEAT VARIETY 25W31

(71) Applicant: Pioneer Hi-Bred International, Inc., Johnston, IA (US)

(72) Inventors: Gregory Charles Marshall, Arcadia, IN (US); William Joseph Laskar, Tipton, IN (US); Kyle Jay Lively, Tipton, IN (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 14/462,679

(22) Filed: Aug. 19, 2014

Related U.S. Application Data

(60) Provisional application No. 61/867,752, filed on Aug. 20, 2013.

(51) Int. Cl.
*A01H 5/10* (2006.01)
*C12N 15/82* (2006.01)
*A01C 1/06* (2006.01)
*A01G 1/00* (2006.01)

(52) U.S. Cl.
CPC .. *A01H 5/10* (2013.01); *A01C 1/06* (2013.01); *A01G 1/001* (2013.01); *C12N 15/8241* (2013.01); *C12N 15/8243* (2013.01); *C12N 15/8245* (2013.01); *C12N 15/8247* (2013.01); *C12N 15/8251* (2013.01); *C12N 15/8271* (2013.01); *C12N 15/8274* (2013.01); *C12N 15/8279* (2013.01); *C12N 15/8286* (2013.01); *C12N 15/8289* (2013.01)

(58) Field of Classification Search
None
See application file for complete search history.

(56) References Cited

U.S. PATENT DOCUMENTS

| | | | |
|---|---|---|---|
| 6,921,852 B2 | 7/2005 | Lively et al. | |
| 6,951,975 B2 | 10/2005 | Marshall et al. | |
| 8,389,831 B2 * | 3/2013 | Lively | A01H 5/10 435/410 |

OTHER PUBLICATIONS

US Plant Variety Protection Certificate No. 20140003 for Wheat Variety 25W31; issued Sep. 26, 2014.
US Plant Variety Protection Certificate No. 200300328 for Wheat Variety 25W41; issued Apr. 13, 2004.
US Plant Variety Protection Certificate No. 200300330 for Wheat Variety 25R35; issued Mar. 19, 2004.

* cited by examiner

*Primary Examiner* — Cynthia Collins
(74) *Attorney, Agent, or Firm* — Pioneer Hi-Bred Int'l, Inc.

(57) ABSTRACT

A wheat variety designated 25W31, the plants and seeds of wheat variety 25W31, methods for producing a wheat plant produced by crossing the variety 25W31 with another wheat plant, and hybrid wheat seeds and plants produced by crossing the variety 25W31 with another wheat line or plant, and the creation of variants by mutagenesis or transformation of variety 25W31. This invention also relates to methods for producing other wheat varieties or breeding lines derived from wheat variety 25W31 and to wheat varieties or breeding lines produced by those methods.

20 Claims, No Drawings

WHEAT VARIETY 25W31

CROSS-REFERENCE TO RELATED APPLICATIONS

The present application claims the benefit of priority to U.S. Provisional Application No. 61/867,752 filed Aug. 20, 2013, the entire disclosure of which is hereby incorporated by reference in its entirety.

FIELD OF THE INVENTION

This invention is in the field of wheat (*Triticum aestivum* L.) breeding, specifically relating to a wheat variety designated 25W31.

BACKGROUND

The present invention relates to a new and distinctive wheat variety designated 25W31, which has been the result of years of careful breeding and selection in a comprehensive wheat breeding program. There are numerous steps involving significant technical human intervention in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These traits may include, but are not limited to higher seed yield, resistance to diseases and/or insects, tolerance to drought and/or heat, altered milling properties, abiotic stress tolerance, improvements in compositional traits, and better agronomic characteristics.

These processes, which lead to the final step of marketing and distribution, can take from approximately six to twelve years of significant technical human intervention starting from the time the first cross is made. Therefore, development of new varieties is a time-consuming process that requires precise forward planning, efficient use of resources, and a minimum of changes in direction. The development of a new variety typically involves the coordinated effort of a team of scientists, including plant breeders, molecular biologists, plant pathologists, entomologists, agronomists, biochemists, bioinformaticians, market analysts, and automation specialists.

Wheat is an important and valuable field crop. Thus, a continuing goal of wheat breeders is to develop stable, high yielding wheat varieties that are agronomically sound. The reasons for this goal are to maximize the amount of grain produced on the land used and to supply food for both animals and humans. To accomplish this goal, the wheat breeder must select and develop wheat plants that have the traits that result in superior varieties.

Wheat is grown worldwide and is the most widely adapted cereal. There are five main wheat market classes. They include the four common wheat (*Triticum aestivum* L.) classes: hard red winter, hard red spring, soft red winter, and white. The fifth class is durum (*Triticum turgidum* L.). Common wheats are used in a variety of food products such as bread, cookies, cakes, crackers, and noodles. In general the hard wheat classes are milled into flour used for breads and the soft wheat classes are milled into flour used for pastries and crackers. Wheat starch is used in the food and paper industries, as laundry starches, and in other products. Because of its use in baking, the grain quality of wheat is very important. To test the grain quality of wheat for use as flour, milling properties are analyzed. Important milling properties are relative hardness or softness, weight per bushel of wheat (test weight), siftability of the flour, break flour yield, middlings flour yield, total flour yield, flour ash content, and wheat-to-flour protein conversion. Good processing quality for flour is also important. Good quality characteristics for flour from soft wheats include low to medium-low protein content, a low water absorption, production of large-diameter test cookies and large volume cakes. Wheat glutenins and gliadins, which together confer the properties of elasticity and extensibility, play an important role in the grain quality. Changes in quality and quantity of these proteins change the end product for which the wheat can be used.

SUMMARY

In certain embodiments, a plant, plant part, seed, or plant cell of wheat variety 25W31 is provided, representative seed of variety 25W31 having been deposited under ATCC accession number PTA-121082.

In certain embodiments, wheat seed is provided from the cross of the plant or plant part of wheat variety 25W31 with a different wheat plant or plant part. Plants and plant parts grown from the seed of the cross are also provided. Methods for producing different wheat plants are provided in which plant breeding techniques are applied to the wheat plant or plant part grown from the seed of the cross.

In certain embodiments, methods for producing progeny seed and the progeny seed so made are provided in which a wheat plant produced by growing a seed of the cross of wheat variety 25W31 with a different wheat plant or plant part is then crossed to a plant of wheat variety 25W31. Methods and backcrossed seed are also provided in which the progeny seed is grown and crossed to a plant wheat variety 25W31 to produce backcrossed seed.

In certain embodiments, methods for producing double haploid wheat plants are provided in which a wheat plant produced by growing a seed of the cross of wheat variety 25W31 with a different wheat plant or plant part is then crossed with another plant to form haploid cells. The chromosomes of the haploid cells are doubled to form double haploid cells which are grown into a double haploid wheat plant or plant part.

In certain embodiments, methods for cleaning, conditioning, or applying a seed treatment to the seed of wheat variety 25W31 are provided.

In certain embodiments, methods of milling the seed of wheat variety 25W31 and the flour produced from such milling is provided. The flour may include a cell of wheat variety 25W31.

In certain embodiments, a tissue culture of cells is provided which are produced from the plant, plant part, seed or cell of wheat variety 25W31. Plants and plant parts regenerated from the tissue culture are also provided.

In certain embodiments, wheat plants are provided which plants include a transgene and which were produced by transforming the plant, plant part, seed or cell of wheat variety 25W31.

In certain embodiments, a plant, plant part, seed, or plant cell of wheat variety 25W31 further comprising a locus conversion is provided. The plant, plant part, seed, or plant cell may have other than the locus conversion essentially all of the morphological and physiological characteristics of wheat variety 25W31. The locus conversion may confer a trait selected from male sterility, abiotic stress tolerance, altered phosphorus, altered antioxidants, altered fatty acids, altered essential amino acids, altered carbohydrates, herbicide resistance, insect resistance, disease resistance or a combination thereof.

In certain embodiments, methods for producing a wheat plant are provided in which plant breeding techniques are applied to a wheat plant grown from seed of wheat variety 25W31 comprising a locus conversion, or to a plant grown from seed of a cross of such a wheat plant to a different wheat plant.

DETAILED DESCRIPTION

Field crops are bred through techniques that take advantage of the plant's method of pollination. A plant is self-pollinated if pollen from one flower is transferred to the same or another flower of the same plant. A plant is sib-pollinated when individuals within the same family or line are used for pollination. A plant is cross-pollinated if the pollen comes from a flower on a different plant from a different family or line. The term cross-pollination herein does not include self-pollination or sib-pollination. Wheat plants (*Triticum aestivum* L.), are recognized to be naturally self-pollinated plants which, while capable of undergoing cross-pollination, rarely do so in nature. Thus intervention for control of pollination is critical to the establishment of superior varieties.

In order to cross pollinate one wheat plant with another to produce progeny with a new combination of genetic traits, a method of cross-pollination is employed. Cross-pollination is known to those skilled in the art. Wheat cross-pollination is achieved by emasculating flowers of a designated female plant and pollinating the female parent with pollen from the designated male parent. The following method was employed to cross-pollinate the wheat plants, but other methods can be used, or modified, as is known to those skilled in the art.

The designated female wheat plant is emasculated before its anthers shed pollen to avoid self-pollination. Emasculation is done by selecting an immature spike on the designated female parent plant that has not started to bloom and shed any viable pollen. Each spike consists of a series of spikelets composed of florets which each contain one ovary with a feathery stigma and three anthers. Typically all but the two primary florets are removed from each spikelet by using tweezers. The glumes of each remaining floret can be trimmed back about 50% using scissors to expose the immature anthers. The tweezers are used to spread the glumes slightly open while at the same time surrounding the anthers. The anthers can then be removed by gently grabbing and pulling them out of the flower with the tweezers in an upward motion. With skill, all three anthers can be removed at once, but this must be confirmed visually before moving to the next flower. Repeated attempts to remove any remaining anthers increases the risk of damage to the stigma and ovary, which will greatly reduce the frequency of cross-pollination. After all the florets are emasculated on a spike, it is covered with a cellophane bag to prevent pollination with stray pollen from surrounding plants. One to three days after the female spike is emasculated a mature spike that is shedding pollen is selected from the designated male plant for cross-pollination using the approach method. The stem of the male spike is cut off at least one foot below the spike and typically the glumes of all the spikelets are trimmed back with scissors to encourage anther extrusion during pollination. The stem of the male spike is placed in a test tube full of water, which is attached to a stick implanted beside the emasculated female spike. The male spike is placed above the emasculated female spike(s) in the same cellophane bag and it is permitted to shed pollen naturally over the next several days. By waiting a few days after emasculation, one can ensure that no anthers or viable pollen has remained in the female spike and the stigmas become more receptive to cross-pollination. Emasculated female spikes that are effectively cross-pollinated by the designated male parent will typically set 10-30 seeds per spike. Depending on the breeding objectives, one to five spikes are typically cross-pollinated for each cross. Spikes from the cross are hand harvested and the F1 seed from the spikes are advanced to the F1 generation. The F1 plants can be used for subsequent cross-pollination or they can be advanced to the F2 generation for selection and further advancement. For the F2 grow out, 2500 to 3500 seeds are typically planted.

A cross between two different homozygous lines produces a uniform population of hybrid plants that may be heterozygous for many gene loci. A cross of two heterozygous plants each that differ at a number of gene loci will produce a population of plants that differ genetically and will not be uniform. Regardless of parentage, plants that have been self-pollinated and selected for type for many generations become homozygous at almost all gene loci and produce a uniform population of true breeding progeny. The term "homozygous plant" is hereby defined as a plant with homozygous genes at 95% or more of its loci.

Choice of breeding or selection methods depends on the mode of plant reproduction, the heritability of the trait(s) being improved, and the type of variety used commercially (e.g., F1 hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. In general breeding starts with the crossing of two genotypes (a "breeding cross"), each of which may have one or more desirable characteristics that is lacking in the other or which complements the other. If the two original parents do not provide all the desired characteristics, other sources can be included by making more crosses. In each successive filial generation, F1→F2; F2→F3; F3→F4; F4→F5, etc., plants are selfed to increase the homozygosity of the line. Typically in a breeding program five or more generations of selection and selfing are practiced to obtain a homozygous plant.

Pedigree breeding is commonly used for the improvement of self-pollinating crops. Two parents that possess favorable, complementary traits are crossed to produce an F1. An F2 population is produced by selfing or sibbing one or several F1's. Selection of the best individuals may begin in the F2 population; then, beginning in the F3, the best individuals in the best families are selected. Replicated testing of families can begin in the F4 generation to improve the effectiveness of selection for traits with low heritability. At an advanced stage of inbreeding (i.e., F5, F6 and F7), the best lines or mixtures of phenotypically similar lines are tested for potential release as new varieties.

Backcross breeding has been used to transfer genes for simply inherited, qualitative, traits from a donor parent into a desirable homozygous variety that is utilized as the recurrent parent. The source of the traits to be transferred is called the donor parent. After the initial cross, individuals possessing the desired trait or traits of the donor parent are selected and then repeatedly crossed (backcrossed) to the recurrent parent. The resulting plant is expected to have the attributes of the recurrent parent (e.g., variety) plus the desirable trait or traits transferred from the donor parent. This approach has been used extensively for breeding disease resistant varieties.

Each wheat breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Various recurrent selection techniques are used to improve quantitatively inherited traits controlled by numerous genes. The use of recurrent selection in self-pollinating crops depends on the ease of pollination and the number of hybrid offspring from each successful cross. Recurrent selection can be used to improve populations of either self- or cross-pollinated crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. Plants from the populations can be selected and selfed to create new varieties.

Another breeding method is single-seed descent. This procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed. In a multiple-seed procedure, wheat breeders commonly harvest one or more spikes (heads) from each plant in a population and thresh them together to form a bulk. Part of the bulk is used to plant the next generation and part is put in reserve. The procedure has been referred to as modified single-seed descent. The multiple-seed procedure has been used to save labor at harvest. It is considerably faster to thresh spikes with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Bulk breeding can also be used. In the bulk breeding method an F2 population is grown. The seed from the populations is harvested in bulk and a sample of the seed is used to make a planting the next season. This cycle can be repeated several times. In general when individual plants are expected to have a high degree of homozygosity, individual plants are selected, tested, and increased for possible use as a variety.

Molecular markers including techniques such as Starch Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs) may be used in plant breeding methods. One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program (Openshaw et al. Marker-assisted Selection in Backcross Breeding. In: Proceedings Symposium of the Analysis of Molecular Marker Data, 5-6 Aug. 1994, pp. 41-43. Crop Science Society of America, Corvallis, Oreg.). The use of molecular markers in the selection process is often called Genetic Marker Enhanced Selection.

The production of double haploids can also be used for the development of homozygous lines in the breeding program. Double haploids are produced by the doubling of a set of chromosomes (1 N) from a heterozygous plant to produce a completely homozygous individual. This can be advantageous because the process omits the generations of selfing needed to obtain a homozygous plant from a heterozygous source. Various methodologies of making double haploid plants in wheat have been developed (Laurie, D. A. and S. Reymondie, *Plant Breeding*, 1991, v. 106:182-189. Singh, N. et al., *Cereal Research Communications*, 2001, v. 29:289-296; Redha, A. et al., *Plant Cell Tissue and Organ Culture*, 2000, v. 63:167-172; U.S. Pat. No. 6,362,393)

Though pure-line varieties are the predominate form of wheat grown for commercial wheat production hybrid wheat is also used. Hybrid wheats are produced with the help of cytoplasmic male sterility, nuclear genetic male sterility, or chemicals. Various combinations of these three male sterility systems have been used in the production of hybrid wheat.

Descriptions of other breeding methods that are commonly used for different traits and crops can be found in one of several reference books (e.g., Allard, *Principles of Plant Breeding*, 1960; Simmonds, *Principles of Crop Improvement*, 1979; editor Heyne, *Wheat and Wheat Improvement*, 1987; Allan, "Wheat", Chapter 18, *Principles of Crop Development*, vol. 2, Fehr editor, 1987).

Promising advanced breeding lines are thoroughly tested and compared to appropriate standards in environments representative of the commercial target area(s). The best lines are candidates for new commercial varieties; those still deficient in a few traits may be used as parents to produce new populations for further selection.

A most difficult task is the identification of individuals that are genetically superior, because for most traits the true genotypic value is masked by other confounding plant traits or environmental factors. One method of identifying a superior genotype is to observe its performance relative to other experimental genotypes and to a widely grown standard variety. Generally a single observation is inconclusive, so replicated observations are required to provide a better estimate of its genetic worth.

A breeder uses various methods to help determine which plants should be selected from the segregating populations and ultimately which lines will be used for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which lines are significantly better or different for one or more traits of interest. Experimental design methods are used to control error so that differences between two lines can be more accurately determined. Statistical analysis includes the calculation of mean values, determination of the statistical significance of the sources of variation, and the calculation of the appropriate variance components. Five and one percent significance levels are customarily used to determine whether a difference that occurs for a given trait is real or due to the environment or experimental error.

Plant breeding is the genetic manipulation of plants. The goal of wheat breeding is to develop new, unique and superior wheat varieties. In practical application of a wheat breeding program, the breeder initially selects and crosses two or more parental lines, followed by repeated selfing and selection, producing many new genetic combinations. The breeder can theoretically generate billions of different genetic combinations via crossing, selfing and mutations.

Each year, the plant breeder selects the germplasm to advance to the next generation. This germplasm is grown under unique and different geographical, climatic and soil conditions, and further selections are then made during and at the end of the growing season.

Proper testing should detect major faults and establish the level of superiority or improvement over current varieties. In addition to showing superior performance, there must be a demand for a new variety. The new variety must be compatible with industry standards, or must create a new market. The introduction of a new variety may incur additional costs to the seed producer, the grower, processor and consumer, for special advertising and marketing, altered seed and commercial production practices, and new product utilization. The testing preceding release of a new variety should take into consideration research and development costs as well as technical superiority of the final variety. It must also be feasible to produce seed easily and economically.

These processes, which lead to the final step of marketing and distribution, can take from six to twelve years from the time the first cross is made. Therefore, development of new varieties is a time-consuming process that requires precise forward planning, efficient use of resources, and a minimum of changes in direction.

Wheat (*Triticum aestivum* L.), is an important and valuable field crop. Thus, a continuing goal of wheat breeders is to develop stable, high yielding wheat varieties that are agronomically sound and have good grain quality for its intended use. To accomplish this goal, the wheat breeder must select and develop wheat plants that have the traits that result in superior varieties.

According to the invention, there is provided a novel wheat variety, designated 25W31 and processes for making 25W31. This invention relates to seed of wheat variety 25W31, to the plants of wheat variety 25W31, to plant parts of wheat variety 25W31, and to processes for making a wheat plant that comprise crossing wheat variety 25W31 with another wheat plant. This invention also relates to processes for making a wheat plant containing in its genetic material one or more traits introgressed into 25W31 through backcross conversion and/or transformation, and to the wheat seed, plant and plant parts produced thereby. This invention also relates to the creation of variants by mutagenesis or transformation of wheat 25W31. This invention further relates to a hybrid wheat seed, plant or plant part produced by crossing the variety 25W31 or a locus conversion of 25W31 with another wheat variety.

Wheat varieties that are highly homogeneous, homozygous and reproducible are useful as commercial varieties. There are many analytical methods available to determine the homozygotic stability, phenotypic stability, and identity of these varieties.

The oldest and most traditional method of analysis is the observation of phenotypic traits. The data is usually collected in field experiments over the life of the wheat plants to be examined. Phenotypic characteristics most often observed are for traits such as seed yield, head configuration, glume configuration, seed configuration, lodging resistance, disease resistance, maturity, etc.

In addition to phenotypic observations, the genotype of a plant can also be examined. There are many laboratory-based techniques available for the analysis, comparison and characterization of plant genotype; among these are Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). Gel electrophoresis is particularly useful in wheat. Wheat variety identification is possible through electrophoresis of gliadin, glutenin, albumin and globulin, and total protein extracts (Bietz, J. A., pp. 216-228, "Genetic and Biochemical Studies of Nonenzymatic Endosperm Proteins" *In Wheat and Wheat Improvement*, ed. E. G. Heyne, 1987).

The variety of the invention has shown uniformity and stability for all traits, as described in the following variety description information. It has been self-pollinated a sufficient number of generations, with careful attention to uniformity of plant type to ensure homozygosity and phenotypic stability. The line has been increased with continued observation for uniformity. No variant traits have been observed or are expected in 25W31, as described in Table 1 (Variety Description Information). Wheat variety 25W31 is a common, soft white winter wheat. Variety 25W31 demonstrates excellent yield potential and test weight, very good straw lodging resistance, very good resistance to leaf rust, very good resistance to *Fusarium* head blight (scab). Variety 25W31 has medium maturity relative to other varieties in the primary region of adaptation. It has shown its best adaptation to the northern soft wheat regions based on tests conducted in Arkansas, Delaware, Indiana, Illinois, Kentucky, Maryland, Michigan, Missouri, Mississippi, Ohio, Pennsylvania, Tennessee, and Ontario, Canada.

Wheat variety 25W31 being substantially homozygous can be reproduced by planting seeds of the line, growing the resulting wheat plants under self-pollinating conditions, and harvesting the resulting seed, using techniques familiar to the agricultural arts.

Wheat variety 25W31 is a soft white winter wheat (*Triticum aestivum* L.) derived from a three parent cross made in 2001 as follows:

W940446G1A/25W41//25R35

W940446G1A, 25W41, and 25R35 are three homozygous lines. First W940446G1A was crossed to 25W41 and then the F1 seed was crossed to 25R35. W940446G1A was a Pioneer experimental line. W940446G1A was a Pioneer experimental line derived from the cross: WBG0198G1/WBL0206D1//2571. Pioneer experimental line WBG0198G1 was derived from the cross: 2548 sib./2555//WBZ053G. WBZ053G was an experimental line derived from the cross: Kavkaz/Hart//2550. Pioneer experimental line WBL0206D1 was derived from the cross: Sumai3/WEF076B1//WEG0065. The cultivar, Sumai3 (PI 481542) is a Chinese line with high levels of resistance to *Fusarium* head blight. Pioneer line WEF076B1 and Pioneer line WEG0065 are backcross derived lines of 2555 with Hessian fly resistance (H13) and Hessian fly resistance (H13) plus powdery mildew resistance (Pm17), respectively. WEF076B1 was derived from the cross 2555*3//2555sib./KS81H1640HF. WEG0065, was derived from the cross 2555*5/Amigo//2555*5/KS81H1640HF. The cultivar KS81H1640HF (Cltr 17960) was a germplasm release from Kansas State University. The detailed parentage of 25W31 is:
2548sib./2555/3/Kavkaz/Hart//2550/5/Sumai3/3/
2555*3//2555sib./KS81H16 40HF /4/ 2555*5/Amigo//
2555*5/KS81H1640HF/6/2571 /7/ 25W41 /8/ 25R35

The single cross W940446G1A/25W41 was made in the 2001 spring greenhouse cycle and was designated W013046. During the 2001 fall greenhouse cycle W013046 was crossed with 25R35 and the final cross was designated W020801.

The subsequent breeding history of 25W31 is described below.

| Year | Generation | Breeding step | Trait Screening |
|---|---|---|---|
| 2001 | Final cross | Final cross made in Windfall, IN. | |
| 2002 | F1 | $F_1$ grown in transplant nursery at Windfall, IN. | |
| 2002-03 | F2 | Bulk population grown and selected at Chatham, Ontario, Canada. Random heads were selected in bulk and advanced to the next generation. | General phenotypic characterization and assessment of overall agronomics and disease resistance. |
| 2003-04 | F3 | Bulk population grown and selected at Chatham, Ontario, Canada. Individual spike selections made and threshed. | General phenotypic characterization and assessment of overall agronomics and disease resistance. |
| 2004-05 | F4 | Headrows from $F_3$ selections grown at Windfall, IN. Individual rows were selected, harvested and threshed individually. | General phenotypic characterization and assessment of overall agronomics and disease resistance. |
| 2005-06 | F5 | A seven row × 3-meter plot was planted at Windfall, IN, Princeton, IN and Chatham, Ontario, Canada. Spikes were harvested from the selected plot in Windfall, IN and threshed individually. | General phenotypic characterization and assessment of overall agronomics and disease resistance. Molecular screen of population for FHB1 (scab resistance) QTL. |
| 2006-07 | F6 | Twenty headrows each of the $F_5$ selection were grown at Windfall, IN and Princeton, IN. Selected rows were cut and threshed individually. This selection was made at Princeton, IN. | General phenotypic characterization and assessment of overall agronomics and disease resistance. |
| 2007-08 | F7 | Preliminary yield testing of an $F_5$ selection from an $F_6$ headrow. This selection designated W020801A2. | Phenotypic characterization: Yield, test weight, harvest moisture, maturity, and resistance to fungal leaf blights present in the field. Grain was tested for total flour yield, breakflour yield, grain protein, lactic acid retention and sucrose retention. Molecular screen of selections for FHB1 (scab resistance) QTL |
| 2008-09 | F8 | Advanced yield testing of W020801A2. 200 individual spikes were harvested from a small bulk increase. | Phenotypic characterization: Yield, test weight, harvest moisture, heading date, plant height, straw lodging resistance, and resistance to *Fusarium* head blight (scab), leaf rust, fungal leaf blights and soil borne mosaic virus diseases that were present in the field. Grain was tested for total flour yield, breakflour yield, grain protein, lactic acid retention and sucrose retention. Molecular screen for FHB1 (scab resistance) QTL |
| 2009-10 | F9 | Elite yield testing of W020801A2. 200 purification headrows planted, off-type rows destroyed prior to maturity. Approximately 100 of the remaining, inside rows were individually cut and threshed. Two spikes were taken from each harvested row. | Phenotypic characterization: Yield, test weight, harvest moisture, heading date, plant height, and resistance to *Fusarium* head blight (scab), powdery mildew, leaf rust, stripe rust, stem rust, fungal leaf blights, spindle streak mosaic virus and soil borne mosaic virus diseases that were present in the field. Grain was tested for total flour yield, breakflour yield, grain protein, lactic acid retention and sucrose retention. |
| 2010-11 | F10 | Elite yield testing continued of W020801A2. Seed from purification headrows planted in individual progeny plots which surrounded 200 headrows. Off-type plots and headrows were destroyed prior to harvest. Equal numbers of spikes were harvested from the remaining progeny plots for a total of 1000 individual spikes. 96 headrows were harvested. The progeny plots were harvested in bulk, which constitutes Breeder Seed. Bulk seed, headrow bulks, and individual spikes were turned over to Pioneer's Supply Management, Parent Wheat Seed group. | Phenotypic characterization: Yield, test weight, harvest moisture, heading date, plant height, straw lodging resistance, and resistance to *Fusarium* head blight (scab), leaf rust, powdery mildew, stripe rust, spindle streak mosaic virus and soil borne mosaic virus diseases that were present in the field. Grain was tested for total flour yield, breakflour yield, grain protein, lactic acid retention and sucrose retention. Molecular screen for FHB1 (scab resistance) QTL |
| 2011-12 | F11 | Elite yield testing continued, designated YW11H. Seed increase continued by Pioneer Parent Wheat Seed Group | Phenotypic characterization: Yield, test weight, harvest moisture, heading date, plant height, and resistance to *Fusarium* head blight (scab), leaf rust, powdery mildew, stripe rust, and barley yellow dwarf virus diseases that were present in the field. Screened for pre-harvest sprouting tolerance. Grain was tested fortotal flour yield, breakflour yield, grain protein, lactic acid retention and sucrose retention. Molecular screen for FHB1 (scab resistance) QTL |

-continued

| Year | Generation | Breeding step | Trait Screening |
|---|---|---|---|
| 2012-13 | F12 | Elite yield testing continued, designated XW11H. Seed increase continued by Pioneer Parent Wheat Seed Group | Phenotypic characterization: Yield, test weight, harvest moisture, heading date, plant height, and resistance to *Fusarium* head blight (scab), leaf rust, powdery mildew, stripe rust, and barley yellow dwarf virus diseases that were present in the field. Screened for pre-harvest sprouting tolerance. Grain was tested for total flour yield, breakflour yield, grain protein, lactic acid retention and sucrose retention. Molecular screen for FHB1 (scab resistance) QTL |

The cultivar 25W31 was bred and selected using a modified pedigree selection method for any and all of the following characteristics in the field environment: disease resistance, plant type, plant height, head type, straw strength, maturity, grain yield, test weight, and milling and baking characteristics.

25W31 has been shown to be uniform and stable since the $7^{th}$ generation, or for the last 5 generations. 25W31 has shown no variants other than what would normally be expected due to environment.

The development of any given wheat variety can take from nine to twelve years or more of significant technical human intervention starting from the time the first cross is made. Therefore, development of new wheat varieties is a time-consuming process that requires precise forward planning, efficient use of resources, and a minimum of changes in direction. The development of a new wheat variety typically involves the coordinated effort of a team of approximately 15 or more scientists, including plant breeders, molecular biologists, plant pathologists, entomologists, agronomists, biochemists, bioinformaticians, market analysts, and automation specialists. These efforts take place in the United States (Arkansas, Delaware, Georgia, Illinois, Indiana, Kentucky, Michigan, Missouri, Mississippi, North Carolina, Ohio, Pennsylvania, Tennessee, Virginia, and Wisconsin.) and Ontario, Canada. Accordingly, the development of 25W31 involved significant technical human intervention.

During the process of development, the plant populations as well as individual plants are evaluated for general health, agronomics, and stability at many stages. These evaluations typically include but are not limited to one or more of the following characteristics: plant architecture traits such as seedling coleoptile length, coleoptile color (presence of anthocyanin), juvenile plant growth habit, tillering, plant height, straw strength or lodging, flag leaf carriage at boot stage, leaf width and length, glaucosity of stems, leaves and spikes, pubescence of leaves and spikes, spike shape, spike density, spike awnedness, and plant color through-out stages of growth; plant growth characteristics, such as vernalization requirement, date for first stem joint emergence, heading date, flowering date, physiological maturity date and harvest maturity; tolerance to weather conditions, such as cold tolerance, resistance to heaving, tolerance to wet soils and standing water, drought and heat tolerance; and grain characteristics, such as grain yield, test weight, 1000 kernel weight, grain moisture, grain color, grain shape, grain protein, flour milling yield and baking characteristics.

During its development, wheat variety 25W31 was assayed and/or planted in field trials and evaluated for a variety of traits and/or characteristics as compared to check varieties. The property(s) of appropriate check varieties include but are not limited to varieties with a similar relative maturity, varieties known to be susceptible to one or more particular diseases, insect, pathogen, field condition, weather condition, soil type or condition, and/or crop management practice, varieties known to be tolerant or resistant to one or more particular diseases, insect, pathogen, field condition, weather condition, soil type or condition, and/or crop management practice, varieties comprising one or more particular marker locus, and/or varieties derived from another appropriate variety or having a particular pedigree. Appropriate choice of check varieties for comparison assures an appropriate baseline and valid qualitative or quantitative assessment of any test varieties.

Throughout the course of the development of 25W31, the plants can be tested for various traits including, but not limited to grain yield, test weight, heading date, harvest maturity, plant height, straw strength, pre-harvest sprout tolerance, resistance levels to leaf rust, stripe rust, tan spot, *Septoria tritici* blotch, *Stagnospora nodorum* blotch, powdery mildew, *Fusarium* (scab), wheat yellow mosaic virus and soilborne mosaic virus, and grain characteristics such as flour yield, flour protein, and baking characteristics.

The resulting line, 25W31, is a high yielding variety. The development of this new wheat line was arduous and lengthy, and involved the cooperation and inventive skill of many scientists, including plant breeders, plant pathologists, and agronomists, over the course of several years. The development of 25W31 involved significant technical human intervention.

The cultivar 25W31 was bred and selected using a modified pedigree selection method for any and all of the following characteristics in the field environment: disease resistance, plant type, plant height, head type, straw strength, maturity, grain yield, test weight, and milling and baking characteristics. 25W31 has been shown to be uniform and stable since the $7^{th}$ generation, or for the last 5 generations. 25W31 has shown no variants other than what would normally be expected due to environment.

Wheat variety 25W31, being substantially homozygous, can be reproduced by planting seeds of the line, growing the resulting wheat plants under self-pollinating or sib-pollinating conditions, and harvesting the resulting seed, using techniques familiar to the agricultural arts.

DEFINITIONS FOR AREA OF ADAPTABILITY

When referring to area of adaptability, such term is used to describe the location with the environmental conditions that would be well suited for this wheat variety. Area of adaptability is based on a number of factors, for example: days to heading, winter hardiness, insect resistance, disease resistance, and drought resistance. Area of adaptability does not indicate that the wheat variety will grow in every location within the area of adaptability or that it will not grow outside the area.

Northern area=States of DE, IL, IN, MI, MO, NJ, NY, OH, PA, WI and Ontario, Canada
Mid-south=States of AR, KY, MO bootheel and TN
Southeast=States of NC, SC, and VA
Deep South=States of AL, GA, LA, and MS

TABLE 1

VARIETY DESCRIPTION INFORMATION
25W31

1. KIND: 1 (1 = Common, 2 = Durum, 3 = Club, 4 = Other)
2. VERNALIZATION: 2 (1 = Spring, 2 = Winter, 3 = Other)
3. COLEOPTILE ANTHOCYANIN: 1 (1 = Absent, 2 = Present)
4. JUVENILE PLANT GROWTH: 2 (1 = Prostrate, 2 = Semi-erect, 3 = Erect)
5. PLANT COLOR (boot stage): 2 (1 = Yellow-Green, 2 = Green, 3 = Blue-Green)
6. FLAG LEAF (boot stage): 2 (1 = Erect, 2 = Recurved)
   FLAG LEAF (boot stage): 2 (1 = Not Twisted, 2 = Twisted)
   FLAG LEAF (boot stage): 2 (1 = Wax Absent, 2 = Wax Present)
7. EAR EMERGENCE: 141 = Number of Days (Average) 2 days later than 25R47
8. ANTHER COLOR: 1 (1 = Yellow, 2 = Purple)
9. PLANT HEIGHT (from soil to top of head, excluding awns): 89 cm (Average) 5 cm taller than 25R47
10. STEM:
    A. ANTHOCYANIN: 1 (1 = Absent, 2 = Present)
    B. WAXY BLOOM: 2 (1 = Absent, 2 = Present)
    C. HAIRINESS (last internode of rachis): 2 (1 = Absent, 2 = Present)
    D. INTERNODE: 1 (1 = Hollow, 2 = Semi-solid, 3 = Solid)
    E. PEDUNCLE: 3 (1 = Erect, 2 = Recurved, 3 = Semi-erect)
    F. AURICLE
       Anthocyanin: 1 (1 = Absent, 2 = Present)
       Hair: 2 (1 = Absent, 2 = Present)
11. HEAD (at maturity)
    A. DENSITY: 2 (1 = Lax, 2 = Middense, 3 = Dense)
    B. SHAPE: 1 (1 = Tapering, 2 = Strap, 3 = Clavate, 4 = Other)
    C. CURVATURE: 2 (1 = Erect, 2 = Inclined, 3 = Recurved)
    D. AWNEDNESS: 4 (1 = Awnless, 2 = Apically Awnletted, 3 = Awnletted, 4 = Awned)
12. GLUMES (at Maturity):
    A. COLOR: 3 -YELLOW (1 = White, 2 = Tan, 3 = Other)
    B. SHOULDER: 2 (1 = Wanting, 2 = Oblique, 3 = Rounded, 4 = Square, 5 = Elevated, 6 = Apiculate)
    C. SHOULDER WIDTH: 1 (1 = Narrow, 2 = Medium, 3 = Wide)
    D. BEAK: 3 (1 = Obtuse, 2 = Acute, 3 = Acuminate)
    E. BEAK WIDTH: 3 (1 = Narrow, 2 = Medium, 3 = Wide)
    F. GLUME LENGTH: 3 (1 = Short (ca. 7 mm), 2 = Medium (ca. 8 mm), 3 = Long (ca. 9 mm))
    G. GLUME WIDTH: 2 (1 = Narrow (ca. 3 mm), 2 = Medium (ca. 3.5 mm), 3 = Wide (ca. 4 mm)
    H. PUBESCENCE: 1 (1 = Not Present 2 = Present)
13. SEED:
    A. SHAPE: 1 (1 = Ovate, 2 = Oval, 3 = Elliptical)
    B. CHEEK: 1 (1 = Rounded, 2 = Angular)
    C. BRUSH: 2 (1 = Short, 2 = Medium, 3 = Long)
       BRUSH: 1 (1 = Not Collared, 2 = Collared)
    D. CREASE: 1 (1 = Width 60% or less of Kernel, 2 = Width 80% or less of Kernel, 3 = Width Nearly as Wide as Kernel) CREASE: 1 (1 = Depth 20% or less of Kernel, 2 = Depth 35%, or less of Kernel, 3 = Depth 50% or less of Kernel)
    E. COLOR: 1 (1 = White, 2 = Amber, 3 = Red, 4 = Other)
    F. TEXTURE: 2 (1 = Hard, 2 = Soft, 3 = Other)
    G. PHENOL REACTION: 4 (1 = Ivory, 2 = Fawn, 3 = Light Brown, 4 = Dark Brown 5 = Black)
    H. SEED WEIGHT: 32 g/1000 Seed
    I. GERM SIZE: 2 (1 = Small, 2 = Midsize, 3 = Large)
14. DISEASE: (0 = Not tested, 1 = Susceptible, 2 = Resistant, 3 = Intermediate, 4 = Tolerant)
    SPECIFIC RACE OR STRAIN TESTED
       Stem Rust (*Puccinia graminis* f. sp. *tritici*): 0
       Leaf Rust (*Puccinia recondita* f. sp. *tritici*): 2
       Stripe Rust (*Puccinia striiformis*): 3
       Loose Smut (*Ustilago tritici*): 0
       Tan Spot (*Pyrenophora tritici-repentis*): 3
       Flag Smut (*Urocystis agropyri*): 0
       Halo Spot (*Selenophoma donacis*): 0
       Common Bunt (*Tilletia tritici* or *T. laevis*): 0
       Septoria nodorum (Glume Blotch): 3
       Dwarf Bunt (*Tilletia controversa*): 0
       Septoria avenae (Speckled Leaf Disease): 0
       Karnal Bunt (*Tilletia indica*): 0
       Septoria tritici (Speckled Leaf Blotch): 3
       Powdery Mildew (*erysiphe graminis* f.sp.*tritici*): 3
       Scab (*Fusarium* spp.): 2
       "Snow Molds":
       "Black Point" (Kernel Smudge): 0
       Common Root Rot (*Fusarium*, *Cochliobolus*, & *Bipolaris* spp.): 0
       Barley Yellow Dwarf Virus (BYDV): 0
       Rhizoctonia Root Rot (*Rhizoctonia solani*): 0
       Soilborne Mosaic Virus (SBMV): 3
       Black Chaff (*Xanthomonas campestris* pv. *translucens*): 0
       Wheat Yellow (Spindle Streak) Mosaic Virus: 0
       Bacterial Leaf Blight (*pseudomonas syringae* pv. *syringae*): 0
       Wheat Streak Mosaic Virus (WSMV): 0
15. INSECT: (0 = Not tested, 1 = Susceptible, 2 = Resistant, 3 = Intermediate, 4 = Tolerant)
    Hessian Fly (*Mayetiola destructor*): 2 Biotype L
    Stem Sawfly (*Cephus* spp): 0
    Cereal Leaf Beetle (*Oulema melanopa*): 0
    Russian Aphid (*Diuraphis noxia*): 0
    Greenbug (*schizaphis graminum*): 0
    Aphids: 0

In one aspect, wheat plants, plant parts and seeds are provided which have all or essentially all of the characteristics set forth in table 1. In one aspect wheat plants, plant parts and seeds are provided which have all or essentially all of the physiological and morphological characteristics of wheat variety 25W31, representative seed having been deposited with the ATCC as disclosed herein.

Further Embodiments of the Invention

Further reproduction of the wheat variety 25W31 can occur by tissue culture and regeneration. Tissue culture of various tissues of wheat and regeneration of plants therefrom is well known and widely published. A review of various wheat tissue culture protocols can be found in "In Vitro Culture of Wheat and Genetic Transformation-Retrospect and Prospect" by Maheshwari et al. (*Critical Reviews in Plant Sciences,* 14(2): pp 149-178, 1995). Thus, another aspect of this invention is to provide cells which upon growth and differentiation produce wheat plants capable of having the physiological and morphological characteristics of wheat variety 25W31.

As used herein, the term plant parts includes plant protoplasts, plant cell tissue cultures from which wheat plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, and the like. The term "plant" includes plant parts. When indicating that a plant is crossed or selfed this indicates that any plant part of the plant can be used. For instance the plant part does not need to be attached to the plant during the crossing or selfing, only the pollen might be used.

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species that are inserted into the genome using transformation are referred to herein collectively as "transgenes". Over the last fifteen to twenty years several methods for producing transgenic plants have been developed, and the present invention, in particular embodiments, also relates to transformed versions of the wheat variety 25W31.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

Various genetic elements can be introduced into the plant genome using transformation. These elements include but are not limited to genes; coding sequences; inducible, constitutive, and tissue specific promoters; enhancing sequences; and signal and targeting sequences.

A genetic trait which has been engineered into a particular wheat plant using transformation techniques, could be moved into another line using traditional breeding techniques that are well known in the plant breeding arts. For example, a backcrossing approach could be used to move a transgene from a transformed wheat plant to an elite wheat variety and the resulting progeny would comprise a transgene. As used herein, "crossing" can refer to a simple X by Y cross, or the process of backcrossing, depending on the context. The term "breeding cross" excludes the processes of selfing or sibbing.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92-6 (1981).

According to a preferred embodiment, the transgenic plant provided for commercial production of foreign protein is a wheat plant. In another preferred embodiment, the biomass of interest is seed. A genetic map can be generated, primarily via conventional RFLP, PCR, and SSR analysis, which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, SNPS and sequencing, all of which are conventional techniques.

Likewise, by means of the present invention, agronomic genes can be expressed in transformed plants. More particularly, plants can be genetically engineered to express various phenotypes of agronomic interest. Through the transformation of wheat the expression of genes can be modulated to enhance disease resistance, insect resistance, herbicide resistance, water stress tolerance and agronomic traits as well as grain quality traits. Transformation can also be used to insert DNA sequences which control or help control male-sterility. DNA sequences native to wheat as well as non-native DNA sequences can be transformed into wheat and used to modulate levels of native or non-native proteins. Anti-sense technology, various promoters, targeting sequences, enhancing sequences, and other DNA sequences can be inserted into the wheat genome for the purpose of modulating the expression of proteins. Exemplary genes implicated in this regard include, but are not limited to, those categorized below.

1. Genes that Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*); McDowell & Woffenden, (2003) Trends Biotechnol. 21(4): 178-83 and Toyoda et al., (2002) Transgenic Res. 11(6):567-82. A plant resistant to a disease is one that is more resistant to a pathogen as compared to the wild type plant.

*Fusarium* head blight along with deoxynivalenol both produced by the pathogen *Fusarium graminearum* Schwabe have caused devastating losses in wheat production. Genes expressing proteins with antifungal action can be used as transgenes to prevent *Fusarium* head blight. Various classes of proteins have been identified. Examples include endochitinases, exochitinases, glucanases, thionins, thaumatin-like proteins, osmotins, ribosome inactivating proteins, flavoniods, lactoferricin. During infection with *Fusarium graminearum* deoxynivalenol is produced. There is evidence that production of deoxynivalenol increases the virulence of the disease. Genes with properties for detoxification of deoxynivalenol (Adam and Lemmens, In International Congress on Molecular Plant-Microbe Interactions, 1996; McCormick et al. Appl. Environ. Micro. 65:5252-5256, 1999) have been engineered for use in wheat. A synthetic peptide that competes with deoxynivalenol has been identified (Yuan et al., Appl. Environ. Micro. 65:3279-3286, 1999). Changing the ribosomes of the host so that they have reduced affinity for deoxynivalenol has also been used to reduce the virulence of the *Fusarium graminearum*.

Genes used to help reduce *Fusarium* head blight include but are not limited to Tri101(*Fusarium*), PDR5 (yeast), tlp-1 (oat), tlp-2(oat), leaf tlp-1 (wheat), tlp (rice), tlp-4 (oat), endochitinase, exochitinase, glucanase (*Fusarium*), permatin (oat), seed hordothionin (barley), alpha-thionin (wheat), acid glucanase (alfalfa), chitinase (barley and rice), class beta II-1,3-glucanase (barley), PR5/tlp (*arabidopsis*), zeamatin (maize), type 1 RIP (barley), NPR1 (*arabidopsis*), lactoferrin (mammal), oxalyl-CoA-decarboxylase (bacterium), IAP (baculovirus), ced-9 (*C. elegans*), and glucanase (rice and barley).

(B) A gene conferring resistance to a pest, such as Hessian fly, wheat, stem sawfly, cereal leaf beetle, and/or green bug. For example the H9, H10, and H21 genes for resistance to Hessian fly.

(C) A gene conferring resistance to disease, including wheat rusts, *Septoria tritici*, *Septoria nodorum*, powdery mildew, *Helminthosporium* diseases, smuts, bunts, *Fusarium* diseases, bacterial diseases, and viral diseases.

(D) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other examples of *Bacillus thuringiensis* transgenes encoding a endotoxin and being genetically engineered are given in the following patents and patent applications and hereby are incorporated by reference for this purpose: U.S. Pat. Nos. 5,188,960; 5,689,052; 5,880,275; WO 91/14778; WO 99/31248; WO 01/12731; WO 99/24581; WO 97/40162 and U.S. application Ser. Nos. 10/032,717; 10/414,637; and 10/606,320.

(E) An insect-specific hormone or pheromone such as an ecdysteroid and juvenile hormone, a variant thereof, a mimetic based thereon, or an antagonist or agonist thereof. See, for example, the disclosure by Hammock et al., *Nature* 344: 458 (1990), of baculovirus expression of cloned juvenile hormone esterase, an inactivator of juvenile hormone.

(F) An insect-specific peptide which, upon expression, disrupts the physiology of the affected pest. For example, see the disclosures of Regan, *J. Biol. Chem.* 269: 9 (1994) (expression cloning yields DNA coding for insect diuretic hormone receptor); Pratt et al., *Biochem. Biophys. Res. Comm.* 163: 1243 (1989) (an allostatin is identified in *Diploptera puntata*); Chattopadhyay et al. (2004) Critical Reviews in Microbiology 30 (1): 33-54 2004; Zjawiony (2004) J Nat Prod 67 (2): 300-310; Carlini & Grossi-de-Sa (2002) Toxicon, 40 (11): 1515-1539; Ussuf et al. (2001) Curr Sci. 80 (7): 847-853; and Vasconcelos & Oliveira (2004) Toxicon 44 (4): 385-403. See also U.S. Pat. No. 5,266,317 to Tomalski et al., who disclose genes encoding insect-specific toxins.

(G) An enzyme responsible for an hyperaccumulation of a monterpene, a sesquiterpene, a steroid, hydroxamic acid, a phenylpropanoid derivative or another non-protein molecule with insecticidal activity.

(H) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene, U.S. application Ser. Nos. 10/389,432, 10/692,367, and U.S. Pat. No. 6,563,020.

(I) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(J) A hydrophobic peptide. See PCT application WO 95/16776 and U.S. Pat. No. 5,580,852 (disclosure of peptide derivatives of Tachyplesin which inhibit fungal plant pathogens) and PCT application WO 95/18855 and U.S. Pat. No. 5,607,914) (teaches synthetic antimicrobial peptides that confer disease resistance).

(K) A membrane permease, a channel former or a channel blocker. For example, see the disclosure by Jaynes et al., *Plant Sci.* 89: 43 (1993), of heterologous expression of a cecropin-beta lytic peptide analog to render transgenic tobacco plants resistant to *Pseudomonas solanacearum*.

(L) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(M) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(N) A virus-specific antibody. See, for example, Tavladoraki et al., *Nature* 366: 469 (1993), who show that transgenic plants expressing recombinant antibody genes are protected from virus attack.

(O) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(P) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(Q) Genes involved in the Systemic Acquired Resistance (SAR) Response and/or the pathogenesis related genes. Briggs, S., Current Biology, 5(2):128-131 (1995), Pieterse & Van Loon (2004) Curr. Opin. Plant Bio. 7(4):456-64 and Somssich (2003) Cell 113(7):815-6.

(R) Antifungal genes (Cornelissen and Melchers, Pl. Physiol. 101:709-712, (1993) and Parijs et al., Planta 183: 258-264, (1991) and Bushnell et al., Can. J. of Plant Path. 20(2):137-149 (1998). Also see U.S. application Ser. No. 09/950,933.

(S) Detoxification genes, such as for fumonisin, beauvericin, moniliformin and zearalenone and their structurally related derivatives. For example, see U.S. Pat. No. 5,792,931.

(T) Cystatin and cysteine proteinase inhibitors. See U.S. application Ser. No. 10/947,979.

(U) Defensin genes. See WO03000863 and U.S. application Ser. No. 10/178,213.

(V) Genes conferring resistance to nematodes. See WO 03/033651 and Urwin et. al., Planta 204:472-479 (1998), Williamson (1999) Curr Opin Plant Bio. 2(4):327-31.

2. Genes that Confer Resistance to a Herbicide, for Example:

(A) Acetohydroxy acid synthase, which has been found to make plants that express this enzyme resistant to multiple types of herbicides, has been introduced into a variety of plants (see, e.g., Hattori et al. (1995) *Mol Gen Genet* 246: 419). Other genes that confer tolerance to herbicides include: a gene encoding a chimeric protein of rat cytochrome P4507A1 and yeast NADPH-cytochrome P450 oxidoreductase (Shiota et al. (1994) *Plant Physiol* 106:17), genes for glutathione reductase and superoxide dismutase (Aono et al. (1995) *Plant Cell Physiol* 36:1687, and genes for various phosphotransferases (Datta et al. (1992) *Plant Mol Biol* 20:619).

(B) A herbicide that inhibits the growing point or meristem, such as an imidazalinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference for this purpose.

(C) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627, 061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491, 288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. Nos. US01/ 46227; 10/427,692 and 10/427,692. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Patent No. 0 242 246 and 0 242 236 to Leemans et al. De Greef et al., *Bio/Technology* 7: 61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose. Exemplary genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(D) A herbicide that inhibits photosynthesis, such as a triazine (psbA and gs+ genes) and a benzonitrile (nitrilase gene). Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825.

3. Genes that Confer or Improve Grain Quality, Such as:

(A) Altered fatty acids, for example, by
(1) Down-regulation of stearoyl-ACP desaturase to increase stearic acid content of the plant. See Knultzon et al., *Proc. Natl. Acad. Sci. USA* 89: 2624 (1992) and WO99/64579 (Genes for Desaturases to Alter Lipid Profiles in Corn),
(2) Elevating oleic acid via FAD-2 gene modification and/ or decreasing linolenic acid via FAD-3 gene modification (see U.S. Pat. Nos. 6,063,947; 6,323,392; 6,372,965 and WO 93/11245),
(3) Altering conjugated linolenic or linoleic acid content, such as in WO 01/12800,
(4) Altering LEC1, AGP, Dek1, Superal1, milps, various Ipa genes such as Ipa1, Ipa3, hpt or hggt. For example, see WO 02/42424, WO 98/22604, WO 03/011015, U.S. Pat. No. 6,423,886, U.S. Pat. No. 6,197,561, U.S. Pat. No. 6,825,397, US2003/0079247, US2003/0204870, WO02/057439, WO03/011015 and Rivera-Madrid, R. et. al. Proc. Natl. Acad. Sci. 92:5620-5624 (1995).

(B) Altered phosphorus content, for example, by the
(1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.
(2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy et al., *Maydica* 35: 383 (1990) and/or by altering inositol kinase activity as in WO 02/059324, US2003/0009011, WO 03/027243, US2003/0079247, WO 99/05298, U.S. Pat. No. 6,197, 561, U.S. Pat. No. 6,291,224, U.S. Pat. No. 6,391,348, WO2002/059324, US2003/0079247, Wo98/45448, WO99/55882, WO01/04147.

(C) Altered carbohydrates effected, for example, by altering a gene for an enzyme that affects the branching pattern of starch or a gene altering thioredoxin (See U.S. Pat. No. 6,531, 648). See Shiroza et al., J. Bacteriol. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtilis* levansucrase gene), Pen et al., Bio/Technology 10: 292 (1992) (production of transgenic plants that express *Bacillus licheniformis* alpha-amylase), Elliot et al., Plant Mol. Biol. 21: 515 (1993) (nucleotide sequences of tomato invertase genes), Søgaard et al., J. Biol. Chem. 268: 22480 (1993) (site-directed mutagenesis of barley alpha-amylase gene), and Fisher et al., Plant Physiol. 102: 1045 (1993) (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US2003/0163838, US2003/0150014, US2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US2004/0025203 (UDPGdH), U.S. Pat. No. 6,194,638 (RGP).

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the barnase and the barstar gene (Paul et al. Plant Mol. Biol. 19:611-622, 1992).

For additional examples of nuclear male and female sterility systems and genes, see also, U.S. Pat. No. 5,859,341; U.S. Pat. No. 6,297,426; U.S. Pat. No. 5,478,369; U.S. Pat. No. 5,824,524; U.S. Pat. No. 5,850,014; and U.S. Pat. No. 6,265, 640; all of which are hereby incorporated by reference.

5. Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821, which are hereby incorporated by reference. Other systems that may be used include the Gin recombinase of phage Mu (Maeser et al., 1991; Vicki Chandler, *The Maize Handbook* ch. 118 (Springer-Verlag 1994), the Pin recombinase of *E. coli* (Enomoto et al., 1983), and the R/RS system of the pSR1 plasmid (Araki et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. No. 5,892,009, U.S. Pat. No. 5,965,705, U.S. Pat. No. 5,929, 305, U.S. Pat. No. 5,891,859, U.S. Pat. No. 6,417,428, U.S. Pat. No. 6,664,446, U.S. Pat. No. 6,706,866, U.S. Pat. No. 6,717,034, U.S. Pat. No. 6,801,104, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, and WO9938977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield. Also see WO0202776, WO2003052063, JP2002281975, U.S. Pat. No. 6,084,153, WO0164898, U.S. Pat. No. 6,177,275, and U.S. Pat. No. 6,107,547 (enhancement of nitrogen utilization and altered nitrogen responsiveness). For ethylene alteration, see US20040128719, US20030166197 and W0200032761. For plant transcription factors or transcriptional regulators of abiotic stress, see e.g. US20040098764 or US20040078852.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. No. 6,794,560, U.S. Pat. No. 6,307,126 (GAI), WO99/09174 (D8 and Rht), and WO2004076638 and WO2004031349 (transcription factors).

7. Genes that Confer Agronomic Enhancements, Nutritional Enhancements, or Industrial Enhancements.

(A) Improved tolerance to water stress from drought or high salt water condition. The HVA1 protein belongs to the group 3 LEA proteins that include other members such as wheat pMA2005 (Curry et al., 1991; Curry and Walker-Simmons, 1993), cotton D-7 (Baker et al., 1988), carrot Dc3 (Seffens et al., 1990), and rape pLEA76 (Harada et al., 1989). These proteins are characterized by 11-mer tandem repeats of amino acid domains which may form a probable amphophilic alpha-helical structure that presents a hydrophilic surface with a hydrophobic stripe (Baker et al., 1988; Dure et al., 1988; Dure, 1993). The barley HVA1 gene and the wheat pMA2005 gene (Curry et al., 1991; Curry and Walker-Simmons, 1993) are highly similar at both the nucleotide level and predicted amino acid level. These two monocot genes are closely related to the cotton D-7 gene (Baker et al., 1988) and carrot Dc3 gene (Seffens et al., 1990) with which they share a similar structural gene organization (Straub et al., 1994). There is, therefore, a correlation between LEA gene expression or LEA protein accumulation with stress tolerance in a number of plants. For example, in severely dehydrated wheat seedlings, the accumulation of high levels of group 3 LEA proteins was correlated with tissue dehydration tolerance (Ried and Walker-Simmons, 1993). Studies on several Indica varieties of rice showed that the levels of group 2 LEA proteins (also known as dehydrins) and group 3 LEA proteins in roots were significantly higher in salt-tolerant varieties compared with sensitive varieties (Moons et al., 1995). The barley HVA1 gene was transformed into wheat. Transformed wheat plants showed increased tolerance to water stress, (Sivamani, E. et al. Plant Science 2000, V.155 p 1-9 and U.S. Pat. No. 5,981,842.)

(B) Another example of improved water stress tolerance is through increased mannitol levels via the bacterial mannitol-1-phosphate dehydrogenase gene. To produce a plant with a genetic basis for coping with water deficit, Tarczynski et al. (Proc. Natl. Acad. Sci. USA, 89, 2600 (1992); WO 92/19731, published No. 12, 1992; Science, 259, 508 (1993)) introduced the bacterial mannitol-1-phosphate dehydrogenase gene, mtlD, into tobacco cells via *Agrobacterium*-mediated transformation. Root and leaf tissues from transgenic plants regenerated from these transformed tobacco cells contained up to 100 mM mannitol. Control plants contained no detectable mannitol. To determine whether the transgenic tobacco plants exhibited increased tolerance to water deficit, Tarczynski et al. compared the growth of transgenic plants to that of untransformed control plants in the presence of 250 mM NaCl. After 30 days of exposure to 250 mM NaCl, transgenic plants had decreased weight loss and increased height relative to their untransformed counterparts. The authors concluded that the presence of mannitol in these transformed tobacco plants contributed to water deficit tolerance at the cellular level. See also U.S. Pat. No. 5,780,709 and international publication WO 92/19731 which are incorporated herein by reference for this purpose.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

Further embodiments of the invention are the treatment of 25W31 with a mutagen and the plant produced by mutagenesis of 25W31. Information about mutagens and mutagenizing seeds or pollen are presented in the IAEA's *Manual on Mutation Breeding* (IAEA, 1977) other information about mutation breeding in wheat can be found in C. F. Konzak, "Mutations and Mutation Breeding" chapter 7B, of *Wheat and Wheat Improvement, 2$^{nd}$* edition, ed. Heyne, 1987.

A further embodiment of the invention is a backcross conversion of wheat variety 25W31. A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to nutritional enhancements, industrial enhancements, disease resistance, insect resistance, herbicide resistance, agronomic enhancements, grain quality enhancement, waxy starch, breeding enhancements, seed production enhancements, and male sterility. Descriptions of some of the cytoplasmic male sterility genes, nuclear male sterility genes, chemical hybridizing agents, male fertility restoration genes, and methods of using the aforementioned are discussed in "Hybrid Wheat by K. A. Lucken (pp. 444-452 In *Wheat and Wheat Improvement*, ed. Heyne, 1987). Examples of genes for other traits include: Leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), Powdery Mildew resistance genes (Pm21), common bunt resistance genes (Bt-10), and wheat streak mosaic virus resistance gene (Wsm1), Russian wheat aphid resistance genes (Dn series such as Dn1, Dn2, Dn4, Dn5), Black stem rust resistance genes (Sr38), Yellow rust resistance genes (Yr series such as Yr1, YrSD, Yrsu, Yr17, Yr15, YrH52), Aluminum tolerance genes (Alt(BH)), dwarf genes (Rht), vernalization genes (Vrn), Hessian fly resistance genes (H9, H10, H21, H29), grain color genes (R/r), glyphosate resistance genes (EPSPS), glufosinate genes (bar, pat) and water stress tolerance genes (Hva1, mtlD). The trait of interest is transferred from the donor parent to the recurrent parent, in this case, the wheat plant disclosed herein. Single gene traits may result from either the transfer of a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest.

Another embodiment of this invention is a method of developing a backcross conversion 25W31 wheat plant that involves the repeated backcrossing to wheat variety 25W31. The number of backcrosses made may be 2, 3, 4, 5, 6 or greater, and the specific number of backcrosses used will depend upon the genetics of the donor parent and whether molecular markers are utilized in the backcrossing program. See, for example, R. E. Allan, "Wheat" in *Principles of Cultivar Development*, Fehr, W. R. Ed. (Macmillan Publishing Company, New York, 1987) pages 722-723, incorporated herein by reference. Using backcrossing methods, one of ordinary skill in the art can develop individual plants and populations of plants that retain at least 70%, 75%, 79%, 80%, 81%, 82%, 83%, 84%, 85%, 86%, 87%, 88%, 89%, 90%, 91%, 92%, 93%, 94%, 95%, 96%, 97%, 98%, or 99% of the genetic profile of wheat variety 25W31. The percentage of the genetics retained in the backcross conversion may be measured by either pedigree analysis or through the use of genetic techniques such as molecular markers or electrophoresis. In pedigree analysis, on average 50% of the starting germplasm would be passed to the progeny line after one cross to another line, 75% after backcrossing once, 87.5% after backcrossing twice, and so on. These percentages are averages and each individual progeny plant may have a different percentage of the parental genome after each cross and/or backcross. And using molecular markers one could determine individuals and select individuals that have a much higher percentage of the recurrent parent at each stage of the backcross process. Molecular markers could also be used to confirm and/or determine the recurrent parent used. Molecular marker assisted breeding or selection may be utilized to reduce the number of backcrosses necessary to achieve the backcross conversion. For example, see Openshaw, S. J. et al., Marker-assisted Selection in Backcross Breeding, In: Proceedings Symposium of the Analysis of Molecular Data, August 1994, Crop Science Society of America, Corvallis, Oreg., where it is demonstrated that a locus conversion can be made in as few as two backcrosses. The backcross conversion or locus conversion developed from this method may be similar to 25W31 for the results listed in Table 1. Such similarity may be measured by a side by side phenotypic comparison, with differences and similarities determined at a 5% significance level. Any such comparison should be made in environmental conditions that account for the trait being transferred. For example, herbicide should not be applied in the phenotypic comparison of herbicide resistant backcross conversion of 25W31 when compared back to 25W31.

Another embodiment of the invention is an essentially derived variety of 25W31 or a locus conversion of 25W31. As determined by the UPOV Convention, essentially derived varieties may be obtained for example by the selection of a natural or induced mutant, or of a somaclonal variant, the selection of a variant individual from plants of the initial variety, backcrossing, or transformation by genetic engineering. An essentially derived variety of 25W31 is further defined as one whose production requires the repeated use of variety 25W31 or is predominately derived from variety 25W31. International Convention for the Protection of New Varieties of Plants, as amended on Mar. 19, 1991, Chapter V, Article 14, Section 5(c). A locus conversion refers to plants within a variety that have been modified in a manner that retains the overall genetics of the variety and further comprises one or more loci with a specific desired trait, such as male sterility, insect, disease or herbicide resistance. Examples of single locus conversions include mutant genes, transgenes and native traits finely mapped to a single locus. One or more locus conversion traits may be introduced into a single wheat variety. As used herein, the phrase 'comprising a' transgene, transgenic event or locus conversion means one or more transgenes, transgenic events or locus conversions.

This invention also is directed to methods for using wheat variety 25W31 in plant breeding.

One such embodiment is the method of crossing wheat variety 25W31 with another variety of wheat to form a first generation population of F1 plants. The population of first generation F1 plants produced by this method is also an embodiment of the invention. This first generation population of F1 plants will comprise an essentially complete set of the alleles of wheat variety 25W31. One of ordinary skill in the art can utilize either breeder books or molecular methods to identify a particular F1 plant produced using wheat variety 25W31, and any such individual plant is also encompassed by this invention. These embodiments also cover use of transgenic or backcross conversions of wheat variety 25W31 to produce first generation F1 plants.

A method of developing a 25W31-progeny wheat plant comprising crossing 25W31 with a second wheat plant and performing a breeding method is also an embodiment of the invention. A specific method for producing a line derived from wheat variety 25W31 is as follows. One of ordinary skill in the art would cross wheat variety 25W31 with another variety of wheat, such as an elite variety. The F1 seed derived from this cross would be grown to form a homogeneous population. The F1 seed would contain one set of the alleles from variety 25W31 and one set of the alleles from the other wheat variety. The F1 genome would be made-up of 50% variety 25W31 and 50% of the other elite variety. The F1 seed would be grown and allowed to self, thereby forming F2 seed. On average the F2 seed would have derived 50% of its alleles from variety 25W31 and 50% from the other wheat variety, but various individual plants from the population would have a much greater percentage of their alleles derived from 25W31 (Wang J. and R. Bernardo, 2000, Crop Sci. 40:659-665 and Bernardo, R. and A. L. Kahler, 2001, Theor. Appl. Genet 102:986-992). The F2 seed would be grown and selection of plants would be made based on visual observation and/or measurement of traits. The 25W31-derived progeny that exhibit one or more of the desired 25W31-derived traits would be selected and each plant would be harvested separately. This F3 seed from each plant would be grown in individual rows and allowed to self. Then selected rows or plants from the rows would be harvested and threshed individually. The selections would again be based on visual observation and/or measurements for desirable traits of the plants, such as one or more of the desirable 25W31-derived traits. The process of growing and selection would be repeated any number of times until a homozygous 25W31-derived wheat plant is obtained. The homozygous 25W31-derived wheat plant would contain desirable traits derived from wheat variety 25W31, some of which may not have been expressed by the other original wheat variety to which wheat variety 25W31 was crossed and some of which may have been expressed by both wheat varieties but now would be at a level equal to or greater than the level expressed in wheat variety 25W31. The homozygous 25W31-derived wheat plants would have, on average, 50% of their genes derived from wheat variety 25W31, but various individual plants from the population would have a much greater percentage of their alleles derived from 25W31. The breeding process, of crossing, selfing, and selection may be repeated to produce another population of 25W31-derived wheat plants with, on average, 25% of their genes derived from wheat variety 25W31, but various individual plants from the population would have a much greater percentage of their alleles derived from 25W31. Another embodiment of the invention is a homozygous 25W31-derived wheat plant that has received 25W31-derived traits.

The modified pedigree selection method of breeding was used to derive this line from elite germplasm. The first cross was made in 1996 and breeding continued until August 2008. 25W31 represents a significant advancement in elite germplasm adapted to the United States and Canada.

The previous example can be modified in numerous ways, for instance selection may or may not occur at every selfing generation, selection may occur before or after the actual self-pollination process occurs, or individual selections may be made by harvesting individual spikes, plants, rows or plots at any point during the breeding process described. In addition, double haploid breeding methods may be used at any step in the process. The population of plants produced at each and any generation of selfing is also an embodiment of the invention, and each such population would consist of plants containing approximately 50% of its genes from wheat variety 25W31, 25% of its genes from wheat variety 25W31 in the second cycle of crossing, selfing, and selection, 12.5% of its genes from wheat variety 25W31 in the third cycle of crossing, selfing, and selection, and so on.

Another embodiment of this invention is the method of obtaining a homozygous 25W31-derived wheat plant by crossing wheat variety 25W31 with another variety of wheat and applying double haploid methods to the F1 seed or F1 plant or to any generation of 25W31-derived wheat obtained by the selfing of this cross.

Still further, this invention also is directed to methods for producing 25W31-derived wheat plants by crossing wheat variety 25W31 with a wheat plant and growing the progeny seed, and repeating the crossing or selfing along with the growing steps with the 25W31-derived wheat plant from 1 to 2 times, 1 to 3 times, 1 to 4 times, or 1 to 5 times. Thus, any and all methods using wheat variety 25W31 in breeding are part of this invention, including selfing, pedigree breeding, backcrossing, hybrid production and crosses to populations. Unique starch profiles, molecular marker profiles and/or breeding records can be used by those of ordinary skill in the art to identify the progeny lines or populations derived from these breeding methods.

Another embodiment of this invention is the method of harvesting the grain of variety wheat variety 25W31 and using the grain as seed for planting. Embodiments include cleaning the seed, treating the seed, and/or conditioning the seed. Cleaning the seed includes removing foreign debris such as weed seed and removing chaff, plant matter, from the seed. Conditioning the seed can include controlling the temperature and rate of dry down and storing seed in a controlled temperature environment. Seed treatment is the application of a composition to the seed such as a coating or powder. Seed material can be treated, typically surface treated, with a composition comprising combinations of chemical or biological herbicides, herbicide safeners, pesticides, insecticides, fungicides, nutrients, germination inhibitors, germination promoters, cytokinins, nutrients, plant growth regulators, antimicrobials, and activators, bactericides, nematicides, avicides, or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council. Some specific seed treatments that may be used on crop seed include, but are not limited to, abscisic acid, acibenzolar-S-methyl, avermectin, amitrol, azaconazole, azospirillum, azoxystrobin, *bacillus, Bacillus subtilis, Bacillus simplex, Bacillus firmus, Bacillus amyloliquefaciens, Pasteuria* genus (e.g. *P. nishizawae*), *bradyrhizobium*, captan, carboxin, chitosan, clothianidin, copper, cyazypyr, difenoconazole, etidiazole, fipronil, fludioxonil, fluquinconazole, flurazole, fluxofenim, GB126, Harpin protein, imazalil, imidacloprid, ipconazole, isofavenoids, lipo-chitooligosaccharide, mancozeb, manganese, maneb, mefenoxam, metalaxyl, metconazole, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendaxole, thiamethoxam, thiocarb, thiram, tolclofos-methyl, triadimenol, *trichoderma*, trifloxystrobin, triticonazole and/or zinc.

It is routine practice to test seed varieties and seeds with specific genetic resistance traits to determine which seed treatment options and application rates will complement such varieties and genetic resistance traits in order to enhance yield. For example, a variety with good yield potential but loose smut susceptibility will benefit from the use of a seed treatment that provides protection against loose smut. Likewise, a variety encompassing a genetic resistance trait conferring insect resistance will benefit from the second mode of action conferred by the seed treatment. Further, the good root establishment and early emergence that results from the proper use of a seed treatment will result in more efficient nitrogen use, a better ability to withstand drought and an overall increase in yield potential of a variety or varieties containing a certain trait when combined with a seed treatment.

Performance Examples of 25W31

In the examples that follow, the traits and characteristics of wheat variety 25W31 are given in paired comparisons with another variety during the same growing conditions and same year. The data collected on each wheat variety is presented for a number of characteristics and traits. (Table 2, Table 3, and Table 4)

The results in Table 2 compare variety 25W31 to varieties 25R47, 25W41, and 25W43 for various agronomic traits. Data in Table 2 was collected at locations in Arkansas, Delaware, Indiana, Illinois, Kentucky, Maryland, Michigan, Missouri, Mississippi, Ohio, Pennsylvania, Tennessee, and Ontario, Canada. The results in Table 3 compare variety 25W31 to varieties 25R47, 25W41, 25W43 for various disease resistance traits. Data in Table 3 was collected at locations in Arkansas, Delaware, Indiana, Illinois, Kentucky, Maryland, Michigan, Missouri, Mississippi, Ohio, Pennsylvania, Tennessee, and Ontario, Canada. The results in Table 4 show values for the grain quality of variety 25W31 and comparison varieties 25R47, 25W41 and 25W43. Quality data were collected from 2009-2013 at the USDA ARS Soft Wheat Quality Lab in Wooster, Ohio.

Table 2

Agronomic trait paired comparisons of 25W31 during the period 2008-2013.

Preliminary yield testing of 25W31 began in the 2007-2008 growing season and wide scale testing has been conducted from the 2008-2009 growing season. It has shown its best adaptation to the northern soft white wheat regions based on tests conducted in Arkansas, Delaware, Indiana, Illinois, Kentucky, Maryland, Michigan, Missouri, Mississippi, Ohio, Pennsylvania, Tennessee, and Ontario, Canada.

| Variety | Grain Yield bu/ac | Test Weight lb/bu | Plant Height cm | Heading Date After Jan 1 | Winter hardiness 1-9@ | Straw Lodging 1-9@ |
|---|---|---|---|---|---|---|
| 2008-13 | | | | | | |
| 25W31 | 94.5 | 59.6 | 88.9 | 141.0 | 7.0 | 7.0 |
| 25R47 | 98.9 | 57.4 | 83.8 | 139.0 | 7.0 | 6.0 |
| Locations | 97 | 97 | 30 | 39 | 7 | 5 |
| Reps. | 191 | 192 | 55 | 82 | 12 | 8 |
| Prob. | 0.0000 | 0.0000 | 0.0000 | 0.0000 | 0.3559 | 0.1592 |
| 2008-11 | | | | | | |
| 25W31 | 97.7 | 60.2 | 96.5 | 147.0 | | 8.0 |
| 25W41 | 91.1 | 58.4 | 88.9 | 145.0 | | 6.0 |
| Locations | 18 | 18 | 4 | 8 | | 2 |
| Reps. | 35 | 35 | 8 | 15 | | 3 |
| Prob. | 0.0017 | 0.0001 | 0.0313 | 0.0007 | | 0.2578 |
| 2008-13 | | | | | | |
| 25W31 | 94.1 | 59.7 | 88.9 | 144.0 | 7.0 | 7.0 |
| 25W43 | 92.6 | 56.4 | 83.8 | 142.0 | 5.0 | 5.0 |
| Locations | 95 | 95 | 26 | 39 | 7 | 5 |
| Reps. | 189 | 191 | 48 | 85 | 12 | 8 |
| Prob. | 0.0655 | 0.0000 | 0.0000 | 0.0000 | 0.0000 | 0.0408 |

@Scale of 1-9 where 9 = excellent or resistant, 1 = poor or susceptible.

Data in above table collected at locations in Arkansas, Delaware, Indiana, Illinois, Kentucky, Maryland, Michigan, Missouri, Mississippi, Ohio, Pennsylvania, Tennessee, and Ontario, Canada.

TABLE 3

Disease trait paired comparisons of 25W31 during the period 2008-2013.

| Variety | Stripe Rust 1-9@ | Leaf Rust 1-9@ | Leaf Blight 1-9@ | Scab 1-9@ | Powdery Mildew 1-9@ | SBMV 1-9@ | SSMV 1-9@ |
|---|---|---|---|---|---|---|---|
| 2008-13 | | | | | | | |
| 25W31 | 5.0 | 7.0 | 6.0 | 8.0 | 6.0 | 5.0 | 5.0 |
| 25R47 | 8.0 | 5.0 | 5.0 | 4.0 | 4.0 | 6.0 | 8.0 |
| Locations | 10 | 18 | 2 | 8 | 7 | 6 | 10 |
| Reps. | 18 | 31 | 4 | 15 | 14 | 9 | 18 |
| Prob. | 0.0002 | 0.0000 | 1.0000 | 0.0000 | 0.0128 | 0.0482 | 0.0002 |
| 2008-11 | | | | | | | |
| 25W31 | | 8.0 | 6.0 | 7.0 | 6.0 | 6.0 | |
| 25W41 | | 2.0 | 5.0 | 4.0 | 5.0 | 7.0 | |
| Locations | | 2 | 2 | 3 | 2 | 3 | |
| Reps. | | 4 | 4 | 6 | 4 | 5 | |
| Prob. | | 0.0255 | 1.0000 | 0.0136 | 0.7048 | 0.0572 | |
| 2008-13 | | | | | | | |
| 25W31 | 5.0 | 7.0 | 6.0 | 8.0 | 6.0 | 5.0 | 5.0 |
| 25W43 | 7.0 | 4.0 | 5.0 | 5.0 | 5.0 | 6.0 | 7.0 |
| Locations | 10 | 16 | 2 | 8 | 6 | 6 | 10 |
| Reps. | 18 | 27 | 4 | 15 | 13 | 9 | 18 |
| Prob. | 0.0005 | 0.0000 | 0.1257 | 0.0004 | 0.1184 | 0.0136 | 0.0005 |

@Scale of 1-9 where 9 = excellent or resistant, 1 = poor or susceptible.
SSMV = Wheat Spindle Streak Mosaic Virus
SBMV = Soil-borne Mosaic Virus.

Data in above table collected at locations in Arkansas, Delaware, Indiana, Illinois, Kentucky, Maryland, Michigan, Missouri, Mississippi, Ohio, Pennsylvania, Tennessee, and Ontario, Canada.

TABLE 4

Average Soft wheat quality data, 2009-2013.

| Variety | Flour Yield % | Break Flour Yield % | Flour Protein % | Lactic Acid SRC % | Sucrose SRC % |
|---|---|---|---|---|---|
| 2009-13 | | | | | |
| 25W31 | 68.5 | 38.4 | 7.8 | 76.7 | 87.2 |
| 25R47 | 71.4 | 45.5 | 6.8 | 85.7 | 83.6 |
| Years | 5 | 5 | 5 | 5 | 5 |
| Reps. | 5 | 5 | 5 | 5 | 5 |
| Prob. | 0.0021 | 0.0012 | 0.0002 | 0.0150 | 0.0493 |
| 2009-11 | | | | | |
| 25W31 | 68.9 | 39.0 | 7.8 | 75.7 | 86.3 |
| 25W41 | 69.6 | 43.1 | 7.5 | 86.4 | 88.4 |
| Years | 3 | 3 | 3 | 3 | 3 |
| Reps. | 3 | 3 | 3 | 3 | 3 |
| Prob. | 0.4524 | 0.0809 | 0.3047 | 0.0134 | 0.6668 |
| 2009-13 | | | | | |
| 25W31 | 68.5 | 38.4 | 7.8 | 76.7 | 87.2 |
| 25W43 | 70.2 | 39.8 | 7.4 | 95.1 | 86.7 |
| Years | 5 | 5 | 5 | 5 | 5 |
| Reps. | 5 | 5 | 5 | 5 | 5 |
| Prob. | 0.0051 | 0.1775 | 0.0226 | 0.0008 | 0.7896 |

Lactic Acid SRC = Lactic Acid Solvent Retention Capacity
Sucrose SRC = Sucrose solution Retention Capacity
Quality data collected at the USDA-ARS Soft Wheat Quality Lab in Wooster, OH 25W31 has demonstrated acceptable soft winter wheat milling and baking qualities.

Examples of Assays Performed to Develop 25W31

The following examples provide descriptions of several assays that can be used to characterize and/or select a wheat variety during one or more stages of variety development. Many other methods and assays are available and can be substituted for, or used in combination with, one or more of the examples provided herein. Tables 1, 2, 3 and 4 provide further information on wheat variety 25W31, which results may be produced from at least one or more assays or methods described in the following examples.

Example 1

Stripe Rust Screening

Stripe rust is a fungal leaf disease that is most common in the mid-southern United States in the early spring. Significant levels of the disease can be found in some seasons anywhere in North America. The infection often mostly occurs on the flag leaf but it may attack the entire plant, including the head. Natural infection of plants in the field may be rated visually using a 1-9 scale, where 1 indicates complete susceptibility and 9 indicates complete resistance. Some major genes for resistance may be detected using controlled seedling screening experiments inoculated with specific races of the pathogen. There are also molecular markers for QTL linked to some specific resistance genes.

Example 2

Leaf Rust Screening

Leaf rust is a fungal leaf disease that is most common in the southern United States in the spring and early summer. Significant levels of the disease can be found in most seasons anywhere in North America. The infection is most damaging when it occurs on the flag leaf but it may attack the entire plant, including the head. Natural infection of plants in the field may be rated visually using a 1-9 scale, where 1 indicates complete susceptibility and 9 indicates complete resistance. Some major genes for resistance may be detected using controlled seedling screening experiments inoculated with specific races of the pathogen. There are also molecular markers for QTL linked to some specific resistance genes.

Example 3

Leaf Blight Screening

Fungal leaf blights, including Tan spot, *Septoria tritici* blotch, and *Stagnospora nodorum* blotch, are common in much of the North American wheat growing regions. The infection is most damaging when it occurs on the flag leaf but it may attack the entire plant, including the head. Natural infection of plants in the field may be rated visually using a 1-9 scale, where 1 indicates complete susceptibility and 9 indicates complete resistance.

Example 4

Scab Screening

*Fusarium* head blight or scab is a fungal disease that is common in much of the North American wheat growing regions. Infection occurs during flowering and is most severe when conditions are wet, warm and remain humid. The disease infects flowers on the spike and will spread to adjacent flowers, often infecting most of the developing kernels on the spike. Natural infection of plants in the field may be rated visually using a 1-9 scale, where 1 indicates complete susceptibility and 9 indicates complete resistance. Infection may be induced in controlled screening experiments where spikes are inoculated with specific spore concentrations of the fungus by spraying the spikes at flowering or injecting the inoculum directly into a flower on each spike. There are also molecular markers for QTL linked to some specific resistance genes.

Example 5

Powdery Mildew Screening

Powdery mildew is a fungal leaf disease that is most common in the southern United States in the spring and early summer. Significant levels of the disease can be found in many seasons anywhere in North America. The infection is most damaging when it occurs on the flag leaf but it may attack the entire plant, including the head. Natural infection of plants in the field may be rated visually using a 1-9 scale, where 1 indicates complete susceptibility and 9 indicates complete resistance. Some major genes for resistance may be detected using controlled seedling screening experiments inoculated with specific races of the pathogen. There are also molecular markers for QTL linked to some specific resistance genes.

Example 6

Soilborne Mosaic Virus Screening

Soilborne mosaic virus is transmitted by the vector, *Polymyxa graminis*, which tends to be most common in low-lying, wet soils; particularly those frequently grown to wheat. Symptoms appear in the spring as light green to yellow mottling along with stunting and resetting plant growth in the most susceptible varieties. Natural infection of plants in the field may be rated visually using a 1-9 scale, where 1 indicates complete susceptibility and 9 indicates complete resistance. Higher levels of natural infection can be induced for screening by planting wheat annually in the same field to increase the vector level.

Example 7

Wheat Yellow (Spindle Streak) Mosaic Virus Screening

Wheat yellow virus is transmitted by the vector, *Polymyxa graminis*, and is most common during cool weather conditions in the spring. Symptoms appear as light green to yellow streaks and dashes parallel to the leaf veins. Symptoms often fade prior to heading as weather conditions become warmer. Natural infection of plants in the field may be rated visually using a 1-9 scale, where 1 indicates complete susceptibility and 9 indicates complete resistance.

Example 8

Flour Yield Screening

The potential average flour yield of wheat can be determined on samples of grain that has been cleaned to standard and tempered to uniform moisture, using a test mill such as the Allis-Chalmers or Brabender mill. Samples are milled to established parameters, the flour sifted into fractions, which are then weighed to calculate flour yield as a percentage of grain weight.

Flour yield "as is" is calculated as the bran weight (over 40 weight) subtracted from the grain weight, divided by grain weight and times 100 to equal "as is" flour yield. Flour yield is calculated to a 15% grain moisture basis as follows: flour moisture is regressed to predict the grain moisture of the wheat when it went into the Quad Mill using the formula Initial grain moisture=1.3429×(flour moisture)−4.

The flour yields are corrected back to 15% grain moisture after estimating the initial grain moisture using the formula Flour Yield$_{(15\%)}$=Flour Yield$_{(as\ is)}$−1.61%×(15%−Actual flour moisture)

Example 9

Flour Protein Screening

The protein content as a percentage of total flour may be estimated by the Kjeldahl method or properly calibrated near-infrared reflectance instruments to determine the total nitrogen content of the flour.

Flour protein differences among cultivars can be a reliable indicator of genetic variation provided the varieties are grown together, but can vary from year to year at any given location. Flour protein from a single, non-composite sample may not be representative. Based on the Soft Wheat Quality Laboratory grow-outs, protein can vary as much 1.5% for a cultivar grown at various locations in the same ½ acre field.

Example 10

Sucrose Solvent Retention Capacity (SRC)

The solvent retention capacity (SRC) of wheat flour measures the ability of the flour to retain various solvents after centrifugation. Sucrose SRC predicts the starch damage and pentosan components, and can be correlated to sugar-snap cookie diameter quality metrics.

Sucrose SRC is a measure of arabinoxylans (also known as pentosans) content, which can strongly affect water absorption in baked products. Water soluble arabinoxylans are thought to be the fraction that most greatly increases sucrose SRC. Sucrose SRC probably is the best predictor of cookie quality, with sugar snap cookie diameters decreasing by 0.07 cm for each percentage point increase in sucrose SRC. The negative correlation between wire-cut cookie and sucrose SRC values is r=−0.66 (p<0.0001). Sucrose SRC typically increases in wheat samples with lower flour yield (r=−0.31) and lower softness equivalent (r=−0.23). The cross hydration of gliadins by sucrose also causes sucrose SRC values to be correlated to flour protein (r=0.52) and lactic acid SRC (r=0.62). Soft wheat flours for cookies typically have a target of 95% or less when used by the US baking industry for biscuits and crackers. Sucrose SRC values increase by 1% for every 5% increase in lactic acid SRC. The 95% target value can be exceeded in flour samples where a higher lactic acid SRC is required for product manufacture since the higher sucrose SRC is due to gluten hydration and not to swelling of the water soluble arabinoxylans.

Example 11

Lactic Acid SRC

Lactic Acid SRC=Lactic Acid Solvent Retention Capacity. Lactic acid SRC measures gluten strength. Typical values are below 85% for "weak" soft varieties and above 105% or 110% for "strong" gluten soft varieties. See the above discussion of protein quality in this section for additional details of the lactic acid SRC. Lactic acid SRC results correlate to the SDS-sedimentation test. The lactic acid SRC is also correlated to flour protein concentration, but the effect is dependent on genotypes and growing conditions. The SWQL typically reports a protein-corrected lactic acid SRC value to remove some of the inherent protein fluctuation not due to cultivar genetics. Lactic acid is corrected to 9% protein using the assumption of a 7% increase in lactic acid SRC for every 1% increase in flour protein. On average across 2007 and 2008, the change in lactic acid SRC value was closer to 2% for every 1% protein.

Example 12

Molecular Screening

As shown in Table 1, plants were analyzed at various times throughout the development of 25W31 for specific alleles for scab resistance. As discussed above, and as is known to those skilled in the art, other traits can also be screened by molecular analysis.

Table 5 lists common traits and a description of how the trait is scored.

Wheat variety 25W31 can be used as the female or the male parent in biparental crosses in order to develop new and valuable wheat varieties. Wheat normally self-pollinates in nature. Wheat cross-pollination can be achieved by emasculating a designated female plant and pollinating the female plant with pollen from the designated male parent.

In order to cross pollinate one wheat plant with another to produce progeny with a new combination of genetic traits, a method of cross-pollination is employed. Cross-pollination is known to those skilled in the art. Wheat cross-pollination is achieved by emasculating flowers of a designated female plant and pollinating the female parent with pollen from the designated male parent. The following method was employed to cross-pollinate the wheat plants, but other methods can be used, or modified, as is known to those skilled in the art.

The designated female wheat plant is emasculated before its anthers shed pollen to avoid self-pollination. Emasculation is done by selecting an immature spike on the designated female parent plant that has not started to bloom and shed any viable pollen. Each spike consists of a series of spikelets composed of florets which each contain one ovary with a feathery stigma and three anthers. Typically all but the two primary florets are removed from each spikelet by using tweezers. The glumes of each remaining floret can be trimmed back about 50% using scissors to expose the immature anthers. The tweezers are used to spread the glumes slightly open while at the same time surrounding the anthers. The anthers can then be removed by gently grabbing and pulling them out of the flower with the tweezers in an upward motion. With skill, all three anthers can be removed at once, but this must be confirmed visually before moving to the next flower. Repeated attempts to remove any remaining anthers increases the risk of damage to the stigma and ovary, which will greatly reduce the frequency of cross-pollination. After all the florets are emasculated on a spike, it is covered with a cellophane bag to prevent pollination with stray pollen from surrounding plants. One to three days after the female spike is emasculated a mature spike that is shedding pollen is selected from the designated male plant for cross-pollination using the approach method. The stem of the male spike is cut off at least one foot below the spike and typically the glumes of all the spikelets are trimmed back with scissors to encourage anther extrusion during pollination. The stem of the male spike is placed in a test tube full of water, which is attached to a stick implanted beside the emasculated female spike. The male spike is placed above the emasculated female spike(s) in the same cellophane bag and it is permitted to shed pollen naturally over the next several days. By waiting a few days after emasculation, one can ensure that no anthers or viable pollen has remained in the female spike and the stigmas become more receptive to cross-pollination.

Emasculated female spikes that are effectively cross-pollinated by the designated male parent will typically set 10-30 seeds per spike. Depending on the breeding objectives, one to five spikes are typically cross-pollinated for each cross. Spikes from the cross are hand harvested and the F1 seed from the spikes are advanced to the F1 generation. The F1 plants can be used for used for subsequent cross-pollination or they can be advanced to the F2 generation for selection and further advancement. For the F2 grow out, 2500 to 3500 seeds are typically planted.

DEPOSIT

Applicant deposited of at least 2500 seeds of Wheat Variety 25W31 with the American Type Culture Collection (ATCC), 10801 University Boulevard, Manassas, Va. 20110 USA, ATCC Deposit No. PTA-121082. The seeds deposited with the ATCC on Mar. 12, 2014 were taken from the seed stock maintained by Pioneer Hi-Bred International, Inc., 7250 NW 62$^{nd}$ Avenue, Johnston, Iowa, 50131 since prior to the filing date of this application. Access to this seed will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. This deposit of the Wheat Variety 25W31 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.). Unauthorized seed multiplication is prohibited.

The foregoing invention has been described in detail by way of illustration and example for purposes of clarity and understanding. However, it will be obvious that certain changes and modifications such as single locus modifications and mutations, somaclonal variants, variant individuals selected from large populations of the plants of the instant variety and the like may be practiced.

The scope of the claims should not be limited by the preferred embodiments set forth in the examples, but should be given the broadest interpretation consistent with the description as a whole.

All publications, patents and patent applications mentioned in the specification are indicative of the level of those skilled in the art to which this invention pertains.

TABLE 5

| TRAIT | DESCRIPTION & HOW SCORED |
|---|---|
| HD DAT | Heading Date in days past Jan. 1st); plot dated on the day when approximately 50% of the heads are 50% out of the boot |
| HGTIN HGTCM | Height (inches or centimeters); scored with a measuring stick after all genotypes fully extended; wheat gathered around stick and average distance to the top of the heads is noted; 2-3 samplings per plot |
| LF BLT | Leaf Blight Complex; score based on amount of infection on flag and flag −1 leaves; typical scale: |

| | % of uninfected leaf surface area | |
|---|---|---|
| | flag | flag −1 |
| | 9 - 100% | 100% |
| | 8 - 100% | 75% |
| | 7 - 100% | 50% |
| | 6 - >90% | <50% |
| | 5 - 75-90% | <25% |
| | 4 - 50-74% | — |
| | 3 - 23-49% | — |
| | 2 - 10-24% | — |
| | 1 - 0-9% | — |

| LF RST | Leaf Rust; score based on amount of infection evident on flag leaves; typical scale:<br>9 - clean<br>8 - trace amounts<br>7 - <5% flag leaf area infected<br>6 - 6-10% "<br>5 - 11-20% "<br>4 - 21-30% "<br>3 - 31-40% "<br>2 - 41-50% "<br>1 - over 50% " |
|---|---|
| MAT | Maturity; used on larger, earlier generation tests in the place of heading date; scale based on maturity of known checks and will vary from year to year based on when the note is taken; typical scale:<br>9 - very late, boot not swelling when note is taken<br>8 - still in boot when note is taken<br>7 - splitting boot, will head two days after note is taken<br>6 - will head day after the note is taken<br>5 - headed on the day note is taken<br>4 - headed day before note taken<br>3 - headed two days before note taken |

TABLE 5-continued

| TRAIT | DESCRIPTION & HOW SCORED |
|---|---|
| | 2 - fully extended, some flowering visible |
| | 1 - extended and flowering |
| | Maturity may also be scored at physiological maturity; typical scaler: |
| | 9 - ready to be harvested |
| | 7 - caryopse hard to divide |
| | 5 - head yellowing an day note is taken |
| | 3 - grain still at dough stage |
| | 1 - head completely green |
| PM | Powdery Mildew; score based on severity of infection and progression of the disease up the plant; scale based on reaction of known checks with attention given to race changes; typical scale: |
| | 9 - clean |
| | 8 - trace amount low on plants |
| | 7 - slight infection mostly low on plants |
| | 6 - moderate infection low on plants; trace amounts on flag −1 leaves |
| | 5 - moderate infection low on plants, moderate amounts on flag −1 leaves |
| | 4 - moderate infection through canopy with trace amounts evident on flag leaves |
| | 3 - severe infection through canopy with up to 25% infection on flag leaves |
| | 2 - severe infection through canopy with up to 50% infection on flag leaves |
| | 1 - severe infection; greater than 50% infection on flag leaves |
| SB MV | Soil Borne Mosaic Virus; score based on amount of mottling, ohlorosis, and/or stunting; scale based on reaction of known checks; typical scale |
| | 1 - severe stunting to the point of rosettes |
| | 2 - severe stunting |
| | 3 - very chlorotic with moderate stunting |
| | 4 - very chlorotic with mild stunting |
| | 5 - moderate mottling with no stunting |
| | 6 - mottling evident |
| | 7 - mottling barely visible |
| | 8 - green, very little mottling |
| | 9 - green, no mottling visible |
| SHTSC | Shattering score. Scores are based on the amount of grain that is visible in the spike just before harvest. |
| | 9 - grain no visible in the spike, Glumes closed. |
| | 8 - Glumes slightly opened in <10% of the grains. |
| | 7 - Glumes slightly opened in >10% of the grains. |
| | 6 - Glumes moderately opened in <20% of the grains. |
| | 5 - Glumes moderately opened in >20% of the grains. |
| | 4 - Glumes completely opened in <30% of the grains. |
| | 3 - Glumes completely opened in >30% of the grains. |
| | 2 - 20%-50% of the grain on the soil |
| | 1 - >50% of the grain on the soil. |
| SS MV | Spindle Streak Mosaic Virus; score based on amount of mottling and chlorosis; scale based on reaction of known checks; scale similar to SS MV with less emphasis on stunting |
| ST EDG | Straw Lodging; score based on amount of lodging; typical scale: |
| | 9 - still upright |
| | 8 - only slight leaning |
| | 7 - some leaning, no lodging |
| | 6 - moderate leaning, little lodging |
| | 5 - up to 10% lodged |
| | 4 - 11-25% lodged |
| | 3 - 26-50% lodged |
| | 2 - 51-75% lodged |
| | 1 - greater than 75% lodged |
| STPRST | Stripe rust. Stripe rust is an important disease that occurs most often in Europe. The infection may only affect the flag leaf, or it may attack the entire plant including the head. Two scales based on level of infection included below: |
| | Score based on the amount of infection of the whole plant! |
| | 9 - clean |
| | 8 - traces |
| | 7 - <5% plant infected |
| | 6 - 10% plant infected |
| | 5 - 20% plant infected |
| | 4 - 40% plant infected |
| | 3 - 60% plant infected |
| | 2 - 60% plant infected head rusted |
| | 1 - Plant not able to produce kernel |
| | Score based on the amount and type of infection evident on flag leaves: |
| | 9 - clean |
| | 8 - trace amounts (Chlorotic-necrotic freckles) |
| | 7 - <5% flag leaf area infected |
| | 6 - 6-10% " (chlorotic-necrotic stripes). |
| | 5 - 11-20% " (chlorotic-necrotic stripes). |
| | 4 - 21-30% " (chlorotic-necrotic stripes). |
| | 3 - 31-40% " (chlorotic-necrotic stripes). |
| | 2 - 41-50% " (some chlorosis). |
| | 1 - over 50% " (no chlorosis). |
| UNI | Uniformity; used to determine how pure a line is generally at the F7 (pre-advanced) generation; typical scale: |
| | 9 - very uniform in all aspects |
| | 8 - good uniformity |
| | 7 - fairly uniform, but some off-types |
| | 6 - several off-types, but can be cleaned up with normal purification procedures |
| | 5 - several off-types, will be a challenge to clean up with normal purification procedures |
| | 4 - considerable number of off-types; will need to be reselected to proceed as a pureline |
| | 3 - as many as 25% off types; will need to be reselected |
| | 2 - as many as 50% off types; will need to be reselected |
| | 1 - more than 50% off types; what you have here is a problem |
| WNTHRD | Winter Hardiness; score based on amount of brownback and kill; best scored at time of early spring regrowth; typical scale: |
| | 9 - very green, no brown-back |
| | 8 - green, slight brown-back |
| | 7 - moderate brown-back |
| | 6 - hard brown-back, no kill |
| | 5 - hard brown-back with less than 10% kill |
| | 4 - 11-25% kill |
| | 3 - 26-50% kill |
| | 2 - 51-75% kill |
| | 1 - greater than 75% kill |
| SC AB | *fusarium* head scab; score based on visual evaluation of the percentage of scab infected heads on a whole plot basis with consideration given to both total heads affected and severity of infection; typical scale: |
| | 9 - no scab infection |
| | 8 - trace amount (1-2%) with infections limited to individual spikelets |
| | 7 - up to 5% infection with most infection limited to less than 50% of the spike |
| | 6 - 5-15% of heads infected |
| | 5 - 15-30% of heads infected |
| | 4 - 30-50% of heads infected |
| | 3 - 50-75% of heads infected |
| | 2 - 75-90% of heads infected |
| | 1 - >90% of heads infected |
| | most genotypes scoring 5 or below would typically have the majority of the spike infected |

What is claimed is:

1. A plant, plant part, seed, or plant cell of wheat variety 25W31, representative seed of said variety having been deposited under ATCC accession number PTA-121082.

2. A wheat seed produced by crossing the plant or plant part of claim 1 with a different wheat plant or plant part.

3. A wheat plant produced by growing the wheat seed of claim 2.

4. A method for producing a second wheat plant comprising applying plant breeding techniques to the wheat plant of claim 3, wherein application of said techniques results in the production of a second wheat plant.

5. A method for producing a progeny seed comprising crossing the wheat plant of claim 3, to a plant of wheat variety 25W31, representative seed of said variety having been deposited under ATCC accession number PTA-121082 and producing a progeny seed.

6. The method of claim 5 further comprising crossing a plant grown from the progeny seed of claim 5 to a plant of wheat variety 25W31 and producing a backcrossed seed.

7. The backcrossed seed produced by claim 6.

8. A method for producing a double haploid wheat plant or plant part comprising a) crossing the wheat plant of claim 3, to another plant to form haploid cells; b) doubling the chromosomes of said haploid cells to form double haploid cells; and c) growing said double haploid cells into a double haploid wheat plant or plant part.

9. A method comprising cleaning the seed of claim 1.

10. A method comprising conditioning the seed of claim 1.

11. A method comprising applying a seed treatment to the seed of claim 1.

12. Flour produced by milling the seed of claim 1.

13. A tissue culture of cells produced from the plant, plant part, seed, or cell of claim 1.

14. A wheat plant regenerated from the tissue culture of claim 13.

15. A wheat plant comprising a transgene wherein said wheat plant was produced by transforming the plant, plant part, seed, or cell of claim 1.

16. A plant, plant part, seed, or plant cell of wheat variety 25W31, representative seed of said variety having been deposited under ATCC accession number PTA-121082, further comprising a locus conversion.

17. The plant, plant part, seed, or plant cell of claim 16, wherein the locus conversion confers a trait selected from the group consisting of male sterility, abiotic stress tolerance, altered phosphorus, altered antioxidants, altered fatty acids, altered essential amino acids, altered carbohydrates, herbicide resistance, insect resistance and disease resistance.

18. A wheat seed produced by crossing the plant of claim 16 with a different wheat plant.

19. A wheat plant produced by growing the wheat seed of claim 18.

20. A method for producing a second wheat plant comprising applying plant breeding techniques to the wheat plant of claim 19, wherein application of said techniques results in the production of a second wheat plant.

* * * * *